(12) United States Patent
Saito et al.

(10) Patent No.: US 7,850,955 B2
(45) Date of Patent: Dec. 14, 2010

(54) GELLING AGENT

(75) Inventors: Keitaro Saito, Kawasaki (JP); Takanori Sugimoto, Kawasaki (JP); Tatsuya Hattori, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 350 days.

(21) Appl. No.: 12/167,556

(22) Filed: Jul. 3, 2008

(65) Prior Publication Data

US 2008/0311164 A1    Dec. 18, 2008

Related U.S. Application Data

(63) Continuation of application No. PCT/JP2007/050370, filed on Jan. 5, 2007.

(30) Foreign Application Priority Data

Jan. 6, 2006    (JP) .............................. 2006-001759

(51) Int. Cl.
| | |
|---|---|
| A61K 31/45 | (2006.01) |
| A61K 31/4015 | (2006.01) |
| A61K 31/164 | (2006.01) |
| C07C 233/05 | (2006.01) |
| C07C 233/63 | (2006.01) |
| C07D 211/40 | (2006.01) |
| C07D 207/38 | (2006.01) |

(52) U.S. Cl. .................... 424/78.03; 514/423; 514/425; 514/348; 548/533; 548/534; 546/296; 516/102; 564/159; 564/199

(58) Field of Classification Search .................. None
See application file for complete search history.

(56) References Cited

U.S. PATENT DOCUMENTS

| 3,969,087 A | 7/1976 | Saito et al. |
| 2002/0159961 A1 | 10/2002 | Yamato et al. |
| 2005/0100572 A1 | 5/2005 | Hatajima et al. |
| 2007/0265347 A1 | 11/2007 | Ueyama et al. |

FOREIGN PATENT DOCUMENTS

| EP | 0 815 833 | 1/1998 |
| JP | 51-19139 | 2/1976 |
| JP | 61-229812 | 10/1986 |
| JP | 6-145141 | 5/1994 |
| JP | 2002-316971 | 10/2002 |
| JP | 2004-123871 | 4/2004 |
| JP | 2005-298387 | 10/2005 |
| WO | 00-53576 | 9/2000 |
| WO | 03-102104 | 12/2003 |
| WO | WO/2004/037159 A2 * | 5/2004 |
| WO | 2004-105707 | 12/2004 |

OTHER PUBLICATIONS

Ferguson, et al., J. Chem. Soc. Perkin Trans. 1. 8:1782 (1980).*
U.S. Appl. No. 12/045,260, filed Mar. 10, 2008, Saito, et al.
B. Rigo, et al., "Studies on Pyrrolidinones. Synthesis of some N-Fatty Acylproglutamic Acids", J. Heterocyclic Chem. 32, pp. 1489-1492 (1995).

* cited by examiner

*Primary Examiner*—Kamal A Saeed
*Assistant Examiner*—Michael Barker
(74) *Attorney, Agent, or Firm*—Oblon, Spivak, McClelland, Maier & Neustadt, L.L.P.

(57) ABSTRACT

Gelling agents which contain a specific N-acylamino acid monoamide monoalkyl ester have a melting temperature of about 100° C., are capable of solidifying a wide variety of oily base materials including silicones, and do not cause "sweating" while retaining a practical level of gel strength. When applied to skin, the resulting gels have a good feeling, good spreadability, and good fittability to skin.

20 Claims, 1 Drawing Sheet

GELLING AGENT

CROSS REFERENCES TO RELATED APPLICATIONS

This application is a continuation of International Patent Application No. PCT/JP2007/050370, filed on Jan. 5, 2007, and claims priority to Japanese Patent Application No. 001759/2006, filed on Jan. 6, 2006, both of which are incorporated herein by reference in their entireties.

BACKGROUND OF THE INVENTION

1. Field of the Invention

The present invention relates to gelling agents. The present invention also relates to gel compositions which containing such a gelling agent. The present invention further relates to novel N-acylamino acid monoamide monoalkyl esters and novel pyrrolidone derivatives.

2. Discussion of the Background

Heretofore, as a gelling agent for water-insoluble oily base materials, generally known are polyamide resin, 12-hydroxystearic acid, fatty acid dextrin, fatty acid inulin, fatty acid glycerin and dibenzylidene-D-sorbitol, which is the condensate of aromatic aldehyde and polyalcohol. However, these gelling agents have a low solubility in oily base materials, and therefore, the dissolving state of the gel composition using them is bad, and the gel composition becomes non-uniform and has a problem in that the gelled oily base material bleeds out of the gel surface owing to the change with time, therefore causing a so-called "sweating phenomenon".

As a gelling agent that has solved these problems, a cosmetic containing an N-acyl-L-glutamic acid dibutylamide has been reported (see, JP-A 51-19139 and JP-A 2002-31697). It is known that it may gel various oily base materials, but its solubility in ordinary oily base materials is low, and when the gelling agent is dissolved, it requires a high temperature of 150° C. or so, and therefore this is not always suitable for the case of incorporating a substance having poor thermal stability and a volatile component.

Thus, a gelling agent having a melting temperature of about 100° C., capable of solidifying a wide variety of oily base materials including silicone, causing no "sweating" while retaining a practical level of gel strength, showing a good feeling during application to skin, concretely showing good gel spreadability, and capable of well fitting to skin is eagerly desired.

SUMMARY OF THE INVENTION

Accordingly, it is one object of the present invention to provide novel gelling agents.

It is another object of the present invention to provide novel gelling agents which have a melting temperature of about 100° C.

It is another object of the present invention to provide novel gelling agents which are capable of solidifying a wide variety of oily base materials.

It is another object of the present invention to provide novel gelling agents which are capable of solidifying a wide variety of oily base materials, including silicones.

It is another object of the present invention to provide novel gelling agents which are capable of forming an excellent gel that causes no "sweating" while retaining a practical level of gel strength.

It is another object of the present invention to provide novel gels which contain or are prepared from such a gelling agent.

It is another object of the preset invention to provide novel compounds which are useful for preparing such a gelling agent and/or gel.

These and other objects, which will become apparent during the following detailed description, have been achieved by the inventors' discovery that these object can be attained by using a specific N-acylamino acid monoamide monoalkyl ester as a gelling agent.

Thus, the present invention provides the following embodiments:

(1) A gelling agent characterized by containing an N-acylamino acid monoamide monoalkyl ester (ingredient A) represented by the following general formula (I):

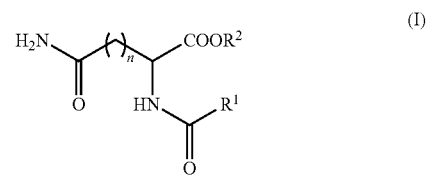

wherein $R^1$ represents a linear or branched hydrocarbon group having from 7 to 17 carbon atoms; $R^2$ represents a linear or branched hydrocarbon group having from 2 to 18 carbon atoms; n indicates 1 or 2.

(2) The gelling agent described in (1), characterized by further containing a glutarimide derivative (ingredient B) represented by the following general formula (II):

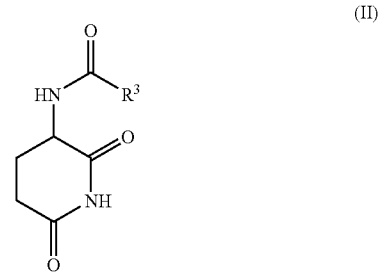

wherein $R^3$ represents a linear or branched hydrocarbon group having from 7 to 17 carbon atoms.

(3) The gelling agent described in any of (1) or (2), characterized by further containing one or two or more selected from a pyrrolidone derivative (ingredient C) represented by the following general formula (III) and an acylglutamic acid diester (ingredient D) represented by the following general formula (IV):

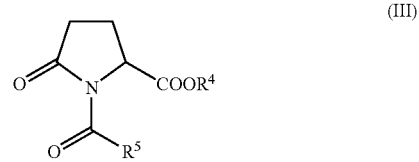

wherein $R^4$ represents a linear or branched hydrocarbon group having from 3 to 6 carbon atoms; $R^5$ represents a linear or branched, saturated hydrocarbon group having from 7 to 17 carbon atoms,

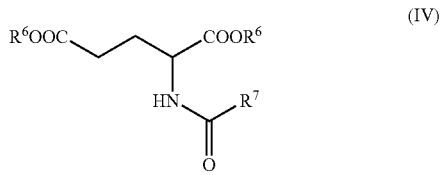

wherein $R^6$ represents a linear or branched hydrocarbon group having from 2 to 6 carbon atoms; $R^7$ represents a linear or branched hydrocarbon group having from 7 to 17 carbon atoms.

(4) A gel composition characterized by containing the gelling agent described in any of (1) to (3) and an oily base material (ingredient E).

(5) An N-acylamino acid monoamide monoalkyl ester (ingredient A) represented by the following general formula (I):

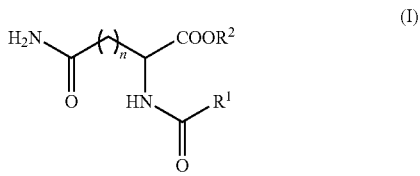

wherein $R^1$ represents a linear or branched hydrocarbon group having from 7 to 17 carbon atoms; $R^2$ represents a linear or branched hydrocarbon group having from 2 to 18 carbon atoms; n indicates 1 or 2.

(6) A pyrrolidone derivative (ingredient C) represented by the following general formula (III):

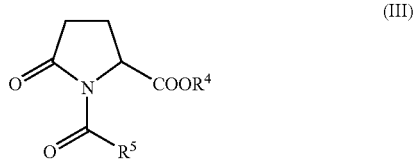

wherein $R^4$ represents a linear or branched hydrocarbon group having from 3 to 6 carbon atoms; $R^5$ represents a linear or branched, saturated hydrocarbon group having from 7 to 17 carbon atoms.

When the specific N-acylamino acid monoamide monoalkyl ester of the invention is used as a gelling agent, it may have a melting temperature of about 100° C., and may solidify a wide variety of oily base materials including a silicone, and can form an excellent gel causing no sweating while retaining a practical level of gel strength.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
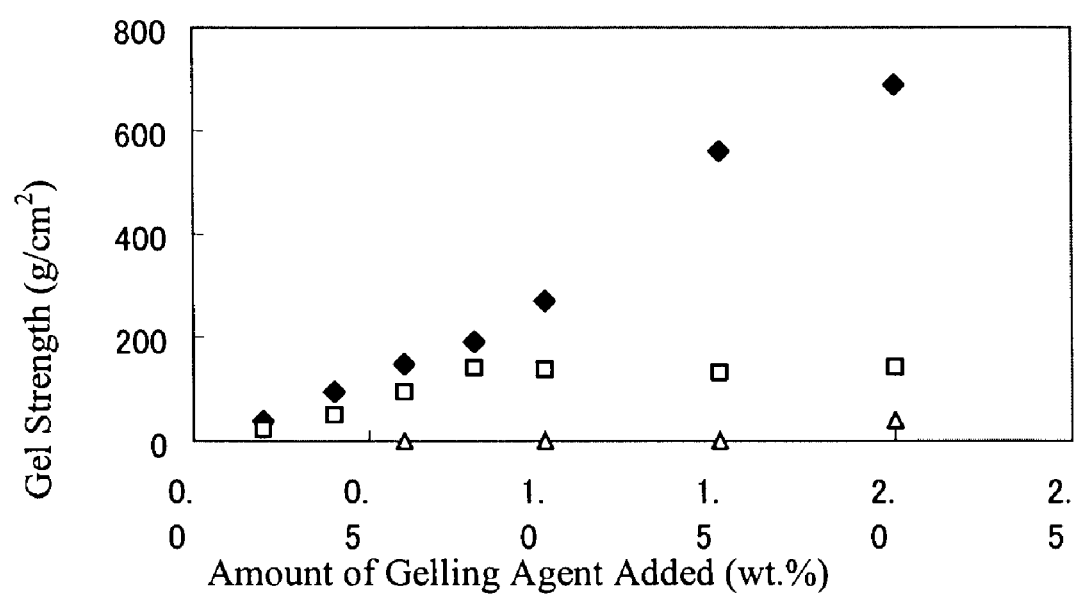
FIG. 1 is a graph showing the relation between the amount of various gelling agents added to liquid paraffin and the gel strength (see, Example 8).

The invention relates to a gelling agent that contains a specific N-acylamino acid monoamide monoalkyl ester (ingredient A). Further, it relates to a gelling agent containing a specific glutarimide derivative (ingredient B), further to a gelling agent containing one or two or more selected from specific pyrrolidone derivatives (ingredient C) or acylglutamic acid diesters (ingredient D), and further to a gel composition containing the gelling agent, a novel N-acylamino acid monoamide monoalkyl ester (ingredient A) and a novel pyrrolidone derivative (ingredient C). These are described in order hereinunder.

The term in the invention, "excellent in the spreadability" means that, when the gel composition is applied to skin, it may readily spread thereon; and "readily fit to skin" means that when the gel composition is applied to skin, it is not repelled but may well fix thereon.

The N-acylamino acid monoamide monoalkyl ester of the ingredient A of the invention is a compound represented by the following general formula (I):

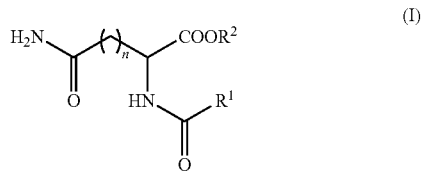

wherein $R^1$ represents a linear or branched hydrocarbon group having from 7 to 17 carbon atoms; $R^2$ represents a linear or branched hydrocarbon group having from 2 to 18 carbon atoms; n indicates 1 or 2.

The hydrocarbon group for $R^1$ may be linear or branched. The long-chain acyl group represented by $R^1$—CO— is an acyl group derived from a saturated or unsaturated fatty acid having from 8 to 18 carbon atoms, and its examples are an octanoyl group, a 2-ethylhexanoyl group, a nonanoyl group, a decanoyl group, a lauroyl group, a myristoyl group, a palmitoyl group, a stearoyl group, an oleoyl group. An acyl group having less than 8 carbon atoms or more than 18 carbon atoms could not exhibit an effective gelling function. It may be an acyl group of a fatty acid having a single composition or may be an acyl group of a naturally-derived mixed fatty acid such as coconut oil fatty acid, castor oil fatty acid, olive oil fatty acid, palm oil fatty acid, or a synthetic fatty acid (including branched fatty acid). One of these may be used singly, or two or more selected from the above groups may be used as combined. From the viewpoint that even a small amount of the ingredient A may be effective for exhibiting an effective gel strength, preferred are a lauroyl group, a myristoyl group, a palmitoyl group, a stearoyl group; more preferred are a lauroyl group, a myristoyl group, a palmitoyl group; even more preferred are a lauroyl group, a palmitoyl group; and still more preferred is a lauroyl group. From the viewpoint of the possibility of forming transparency with retaining the gel strength, it is desirable to mix two or more those groups and use them. More preferred is mixing and using at least two selected from a group selected from a lauroyl group, a myristoyl group, a palmitoyl group and a stearoyl group; even more preferred is mixing and using at least two selected from a lauroyl group, a myristoyl group and a palmitoyl group; and still more preferred is mixing and using a lauroyl group and a palmitoyl group. For attaining the above-mentioned object, an acyl group of coconut oil fatty acid may also be used.

$R^2$ represents a linear or branched hydrocarbon group having from 2 to 18 carbon atoms; and when $R^2$ is a hydrogen atom or has more than 18 carbon atoms, then the agent could not have a sufficient gelling potency. One such group may be used singly, or two or more selected from the above-mentioned groups may be mixed and used. From the viewpoint that even a small amount of the ingredient A may be effective for exhibiting an effective gel strength, preferred is a linear or branched hydrocarbon group having from 3 to 12 carbon atoms, more preferred is a linear or branched hydrocarbon group having from 3 to 8 carbon atoms, even more preferred is a branched hydrocarbon group having from 3 to 8 carbon atoms, and still more preferred is a t-butyl group, a sec-butyl group or an isopropyl group, and further more preferred is an isopropyl group.

The amino acid for the ingredient A of the invention is glutamine or asparagine. It may be a DL-form, or an optically-active form such as an L-form or a D-form. Concretely, it includes DL-glutamine, D-glutamine, L-glutamine, DL-asparagine, D-asparagine, L-asparagine. One of these may be used singly, or two or more selected from the above groups may be combined and used herein. From the viewpoint of exhibiting a stable gelling capability, preferred is an optically-active glutamine or asparagine, more preferred is D-glutamine or L-glutamine, and even more preferred is L-glutamine.

The ingredient A of the invention includes N-lauroylglutamine isopropyl ester, N-lauroylglutamine sec-butyl ester, N-lauroylglutamine ethyl ester, N-lauroylglutamine n-octyl ester, N-lauroylglutamine lauryl ester, N-palmitoylglutamine isopropyl ester, N-palmitoylglutamine sec-butyl ester, N-palmitoylglutamine ethyl ester, N-myristoylglutamine sec-butyl ester, N-myristoylglutamine isopropyl ester, N-myristoylglutamine ethyl ester, N-stearoylglutamine sec-butyl ester, N-stearoylglutamine isopropyl ester. From the viewpoint that even a small amount of the ester may be effective for exhibiting an effective gel strength, preferred are N-lauroylglutamine isopropyl ester, N-lauroylglutamine sec-butyl ester, N-lauroylglutamine n-octyl ester, more preferred are N-lauroylglutamine isopropyl ester, N-lauroylglutamine sec-butyl ester; and still more preferred is N-lauroylglutamine isopropyl ester.

The ingredient A of the invention may be prepared by a combination of known techniques. For example, an N-acylglutamine or N-acylasparagine is prepared by Schotten-Baumann reaction of reacting a long-chain fatty acid halide and glutamine or asparagine in the presence of a basic catalyst, then this is further reacted under heat with an alcohol in the presence of an acid catalyst or in the absence of the catalyst, thereby giving it.

The ingredient A of the invention may be used as a gelling agent for oily base materials. It has a melting temperature of 100° C. or so, and may solidify a wide variety of oily base materials including silicone, and may form an excellent gel causing no "sweating" while retaining a practical level of gel strength.

An ingredient generally usable in cosmetics may be incorporated in the gelling agent of the invention, not detracting from the advantage of the invention. Not specifically defined, the ratio of the ingredient A to the whole gelling agent may be any one that secures gellation. From the viewpoint that even a small amount the ingredient may exhibit the gelling effect, the lowermost limit of the ingredient A/gelling agent (% by weight) is preferably 30% by weight, more preferably 50% by weight, even more preferably 70% by weight, still more preferably 90% by weight, especially more preferably 95% by weight. From the viewpoint of most efficiently exhibiting the gelling capability, the uppermost limit is preferably 100% by weight, more preferably 99.9% by weight.

In addition to the ingredient A, a specific glutarimide derivative (ingredient B) may be further incorporated in the gelling agent of the invention, thereby preparing a gel that has excellent spreadability while retaining the strength.

The glutarimide derivative of the ingredient B in the invention is a compound represented by the following general formula (II):

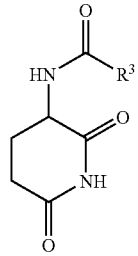

(II)

wherein $R^3$ represents a linear or branched hydrocarbon group having from 7 to 17 carbon atoms.

In the formula, $R^3$ represents a linear or branched hydrocarbon group having from 7 to 17 carbon atoms. The hydrocarbon group for $R^3$ may be linear or branched. The long-chain acyl group represented by $R^3$—CO— is an acyl group derived from a saturated or unsaturated fatty acid having from 8 to 18 carbon atoms, including, for example, an octanoyl group, a 2-ethylhexanoyl group, a nonanoyl group, a decanoyl group, a lauroyl group, a myristoyl group, a palmitoyl group, a stearoyl group, an oleoyl group. It may be an acyl group of a fatty acid having a single composition or may be an acyl group of a naturally-derived mixed fatty acid such as coconut oil fatty acid, castor oil fatty acid, olive oil fatty acid, palm oil fatty acid, or a synthetic fatty acid (including branched fatty acid). One of these may be used singly, or two or more selected from the above groups may be used as combined.

The ingredient B in the invention includes 2-(octanoylamino)glutarimide, 2-(decanoylamino)glutarimide, 2-(lauroylamino)glutarimide, 2-(2-ethylhexanoylamino)glutarimide, 2-(myristoylamino)glutarimide, 2-(palmitoylamino)glutarimide. From the viewpoint of the ability to efficiently impart excellent spreadability while retaining the strength of the gelling agent, preferred are 2-(lauroylamino)glutarimide and 2-(2-ethylhexanoylamino)glutarimide, and more preferred is 2-(lauroylamino)glutarimide.

The ingredient B in the invention may be prepared by a combination of known techniques. For example, an N-acylglutamine is prepared by Schotten-Baumann reaction of reacting a long-chain fatty acid halide and glutamine in the presence of a basic catalyst, and then this is processed with a peptide condensing agent such as diisopropylcarbodiimide or dicyclohexylcarbodiimide, thereby giving it.

The ingredient B in the invention may be a racemic form (DL form) or an optically-active form such as an L-form or a D-form. Those having a high enantiomer excessive ratio are preferred; a D-form or an L-form is more preferred; and an L-form is even more preferred.

Not specifically defined, the blend ratio of the ingredient A and the ingredient B in the invention may be any one that secures gellation. From the viewpoint that the formed gel may noticeably exhibit its spreadability, the lowermost limit of the ingredient B/ingredient A (% by weight) is preferably 0.01% by weight, more preferably 0.1% by weight, even more preferably 0.3% by weight, still more preferably 0.5% by weight, further more preferably 1% by weight, still further preferably 5% by weight, especially preferably 10% by weight. On the other hand, from the viewpoint that it has no influence on the gel strength and the spreadability can be effectively exhibited, the uppermost limit of the ingredient B/ingredient A (% by weight) is preferably 50% by weight, more preferably 40% by weight, even more preferably 30% by weight, still more preferably 20% by weight.

The gelling agent of the invention may further contain one or two or more selected from specific pyrrolidone derivatives (ingredient C) or specific acylamino acid diesters (ingredient D), in addition to the ingredient A and the ingredient B, thereby preparing a gel having excellent spreadability and capable of well fitting to skin while retaining the strength.

The pyrrolidone derivative of the ingredient C of the invention is a compound represented by the following general formula (III):

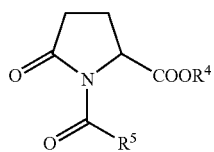

(III)

wherein $R^4$ represents a linear or branched hydrocarbon group having from 3 to 6 carbon atoms; $R^5$ represents a linear or branched, saturated hydrocarbon group having from 7 to 17 carbon atoms.

$R^4$ is a linear or branched hydrocarbon group having from 3 to 6 carbon atoms; and when $R^4$ is a hydrogen atom or a methyl group or an ethyl group, then it is unfavorable since the stability of the compound is problematic. On the other hand, when the number of the carbon atoms is more than 6, then it is unfavorable since the production process may be difficult. Preferred embodiments of $R^4$ are an isopropyl group, a sec-butyl group; and more preferred is an isopropyl group.

$R^5$ may be any of a linear or branched, saturated hydrocarbon group having from 7 to 17 carbon atoms. The long-chain acyl group represented by $R^5$—CO— is an acyl group derived from a saturated fatty acid having from 8 to 18 carbon atoms, and its examples are an octanoyl group, a 2-ethylhexanoyl group, a nonanoyl group, a decanoyl group, a lauroyl group, a myristoyl group, a palmitoyl group, a stearoyl group.

The ingredient C of the invention includes isopropyl N-lauryl-2-pyrrolidone-5-carboxylate, isopropyl N-palmitoyl-2-pyrrolidone-5-carboxylate, isopropyl N-myristoyl-2-pyrrolidone-5-carboxylate, sec-butyl N-lauroyl-2-pyrrolidone-5-carboxylate. From the viewpoint of the excellent fittability to skin and the easiness in production thereof, preferred are isopropyl N-myristoyl-2-pyrrolidone-5-carboxylate, isopropyl N-lauroyl-2-pyrrolidone-5-carboxylate; and more preferred is isopropyl N-lauroyl-2-pyrrolidone-5-carboxylate.

The ingredient C of the invention may be prepared by a combination of known techniques. For example, it may be produced according to the following method:

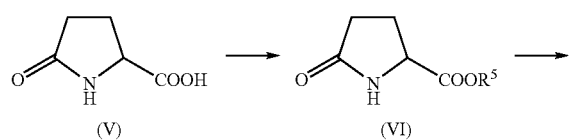

-continued

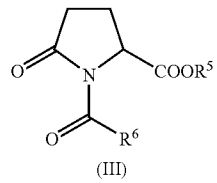

(III)

wherein $R^5$ and $R^6$ have the same meanings as above.

First, pyrrolidone-carboxylic acid (V) is esterified with thionyl chloride or the like to give an intermediate (VI), and then this is acylated with an acid chloride in the presence of a base such as triethylamine to produce the intended ingredient C.

The ingredient C of the invention may be any a racemic form (DL form) or an optically-active form such as an L-form or a D-form, and any of them is usable. Those having a high enantiomer excessive ratio are preferred; a D-form or an L-form is more preferred; and an L-form is even more preferred.

Not specifically defined, the blend ratio of the ingredient C to the ingredient A in the invention may be any one that secures gellation. From the viewpoint that the formed gel may noticeably exhibit its ability to readily fit to skin, the lowermost limit of the ingredient C/ingredient A (% by weight) is preferably 0.01% by weight, more preferably 0.1% by weight, even more preferably 0.3% by weight, still more preferably 0.5% by weight, further more preferably 1% by weight, still further preferably 5% by weight, especially preferably 10% by weight. On the other hand, from the viewpoint that it has no influence on the gel strength and that the gel may effectively exhibit its ability to readily fit to skin, the uppermost limit of the ingredient C/ingredient A (% by weight) is preferably 1000% by weight, more preferably 100% by weight, even more preferably 50% by weight, still more preferably 20% by weight.

The acylglutamic acid diester of the ingredient D in the invention is a compound represented by the following general formula (IV):

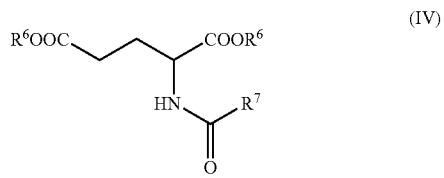

(IV)

wherein $R^6$ represents a linear or branched hydrocarbon group having from 2 to 6 carbon atoms; $R^7$ represents a linear or branched hydrocarbon group having from 7 to 17 carbon atoms.

The ingredient D in the invention includes isopropyl N-lauroylglutamate, Sec-butyl N-lauroylglutamate, n-butyl N-lauroylglutamate, octyl N-lauroylglutamate, 2-ethylhexyl N-lauroylglutamate, isopropyl N-myristoylglutamate, sec-butyl N-myristoylglutamate.

The ingredient D in the invention may be prepared by a combination of known techniques. For example, an N-acyl-acidic amino acid is prepared by Schotten-Baumann reaction of reacting a long-chain fatty acid halide and an acidic amino acid in the presence of a basic catalyst, and then this is reacted under heat with an alcohol in the presence of an acid catalyst or in the absence of a catalyst, thereby giving it. The N-acyl-acidic amino acid may be prepared according to known esterification.

The ingredient D in the invention may be a racemic form (DL form) or an optically-active form such as an L-form or a D-form. Those having a high enantiomer excessive ratio are preferred; a D-form or an L-form is more preferred; and an L-form is even more preferred.

Not specifically defined, the blend ratio of the ingredient D to the ingredient A in the invention may be any one that secures gellation. From the viewpoint that the formed gel may noticeably exhibit its ability to readily fit to skin, the lowermost limit of the ingredient D/ingredient A (% by weight) is preferably 0.01% by weight, more preferably 0.1% by weight, even more preferably 0.3% by weight, still more preferably 0.5% by weight, further more preferably 1% by weight, still further preferably 5% by weight, especially preferably 10% by weight. On the other hand, from the viewpoint that it has no influence on the gel strength and that the gel may effectively exhibit its ability to readily fit to skin, the uppermost limit of the ingredient D/ingredient A (% by weight) is preferably 1000% by weight, more preferably 100% by weight, even more preferably 50% by weight, still more preferably 20% by weight.

The gelling agent of the invention includes the gelling agent containing the ingredient A, the gelling agent containing the ingredients A and B, the gelling agent containing the ingredients A and C, the gelling agent containing the ingredients A and D, the gelling agent containing the ingredients A, B and C, the gelling agent containing the ingredients A, B and D, and the gelling agent containing the ingredients A, B, C and D. In particular, from the viewpoint that a gel having excellent spreadability and readily fittable to skin while retaining the gel strength, preferred are the gelling agent containing the ingredients A, B and C, the gelling agent containing the ingredients A, B and D, and the gelling agent containing the ingredients A, B, C and D; and more preferred is the gelling agent containing the ingredients A, B, C and D.

When combined with any other gelling agent, the gelling agent of the invention may have an enhanced gel strength. Not specifically defined, the other gelling agent usable herein includes, for example, polyamide resin, 12-hydroxystearic acid, sodium stearate, dibenzylidene-D-sorbitol, fatty acid dextrin, fatty acid glycerin, acylglutamic acid diamides such as N-2-ethylhexyl-L-glutamic acid dibutylamide, N-lauroyl-L-glutamic acid dibutylamide, and acylamino acids such as N-lauroyl-L-alanine, etc. From the viewpoint that a transparent gel can be formed as a synergistic effect, preferred are acylglutamic acid diamides and acylamino acids; more preferred are acylglutamic acid diamides; even more preferred are N-2-ethylhexyl-L-glutamic acid dibutylamide, N-lauroyl-L-glutamic acid dibutylamide; and still more preferred is N-2-ethylhexyl-L-glutamic acid dibutylamide.

The amount of the other gelling agent relative to the ingredient A is not specifically defined. From the viewpoint of the capability of imparting transparency, it is preferably used in an amount to fall within a range of from 20% to 500%, more preferably from 50% to 200%, even more preferably from 75% to 150%, still more preferably from 90% to 110%, further more preferably from 95% to 105%.

Ingredients generally usable in cosmetics such as various chelating agents, antiperspirant active ingredients, surfactants, various additives and various powders may be incorporated in the gelling agent of the invention, not detracting from the advantage of the invention.

Not specifically defined, the amount of the ingredient A in the whole gelling agent may be any one that secures gellation. From the viewpoint that even a small amount of the gelling agent may exhibit its gelling effect, the lowermost limit of the ingredient A/gelling agent (% by weight) is preferably 30% by weight, more preferably 50% by weight, even more preferably 70% by weight, still more preferably 90% by weight, further more preferably 95% by weight. From the viewpoint that the gelling agent may most efficiently exhibit its gelling capability, the uppermost limit is preferably 100% by weight.

When the gelling agent of the invention is reacted with an oily base material (ingredient E), its melting point is 100° C. or so and it may solidify a wide variety of oily base materials including silicone, therefore providing an excellent gel composition causing no "sweating" while retaining a practical level of gel strength.

Not specifically defined, the oily base material (ingredient E) usable in the gel composition of the invention may be any one capable of sufficiently dissolving the above-mentioned gelling agent and, when cooled to room temperature, capable of forming a gel. Concretely, it includes silicone oils such as methylpolysiloxane, polyoxyethylene/methylpolysiloxane copolymer, polyoxypropylene/methylpolysiloxane copolymer, poly(oxyethylene, oxypropylene)/methylpolysiloxane copolymer, stearoxymethylpolysiloxane, stearoxytrimethylsilane, methylhydrogenpolysiloxane, octamethylpolysiloxane, decamethylpolysiloxane, decamethylcyclopentasiloxane, octamethylcyclotetrasiloxane, tetrahydrotetramethylcyclotetrasiloxane, methylcyclopolysiloxane, cyclopentasiloxane, dodecamethylcyclohexasiloxane, methylphenylpolysiloxane, trimethylsiloxysilicic acid, aminoethylaminopropylsiloxane/dimethylsiloxane, silanol-modified polysiloxane, alkoxy-modified polysiloxane, fatty acid-modified polysiloxane, fluorine-modified polysiloxane, epoxy-modified polysiloxane, alkoxy-modified polysiloxane, perfluoropolyether, polyvinyl acetate dimethylpolysiloxane; higher alcohols such as cetyl alcohol, isostearyl alcohol, lauryl alcohol, hexadecyl alcohol, octyldodecanol; fatty acids such as isostearic acid, undecylenic acid, oleic acid; polyalcohols such as glycerin, sorbitol, ethylene glycol, propylene glycol, polyethylene glycol; esters such as myristyl myristate, hexyl laurate, decyl oleate, isopropyl myristate, hexyldecyl dimethyloctanoate, glycerin monostearate, diethyl phthalate, ethylene glycol monostearate, octyl hydroxystearate, alkyl benzoate; hydrocarbons such as liquid paraffin, polyisobutene, Vaseline, squalane; waxes such as lanolin, reduced lanolin, carnauba wax; oils and fats such as mink oil, cacao oil, palm oil, palm kernel oil, camellia oil, sesame oil, castor oil, olive oil; ethylene/α-olefin cooligomer, etc. Above all, silicone oils are preferred.

Not specifically defined, the amount of the gelling agent to be in the gel composition of the invention may be any one capable of gelling the oily base material therein. From the viewpoint of obtaining a practical gel composition, the lowermost limit of the amount of the gelling agent relative to the whole gel composition (% by weight) is preferably 0.01% by weight, more preferably 0.1% by weight, even more preferably 0.3% by weight, still more preferably 1% by weight, further more preferably 3% by weight, especially preferably 5% by weight.

From the viewpoint of obtaining the gel composition, the uppermost limit of the amount of the gelling agent relative to the whole gel composition (% by weight) is preferably 50% by weight, more preferably 30% by weight, even more preferably 20% by weight, still more preferably 15% by weight, further preferably 10% by weight.

Not specifically defined, the oily base agent (ingredient E) for use in the gel composition of the invention may be any one that secures gellation. The lowermost limit of the amount of the oily base material relative to the whole gel composition (% by weight) is, from the viewpoint of forming a gel network and retaining it, preferably 10% by weight, more preferably 30% by weight, even more preferably 50% by weight, still more preferably 70% by weight, further more preferably 90% by weight. The uppermost limit of the amount of the oily base material relative to the whole gel composition (% by weight) is, from the viewpoint of efficiently forming a gel, preferably 99.9%, more preferably 99%, even more preferably 98%.

Ingredients generally usable in cosmetics such as various chelating agents, antiperspirant active ingredients, surfactants, various additives and various powders may be incorporated in the gel composition of the invention, not detracting from the advantage of the invention. The gel composition means, in a narrow sense thereof, a composition comprising only the gelling agent and an oily base material, but in a broad sense thereof, it may include cosmetics, aromatics and quasi drugs as final products further containing additives.

As various additives, preferred are, though not specifically defined, chelating agents selected from a group consisting of triethylenetetramine, 2-tenoyltrifluoroacetone, thioglycolic acid, tartaric acid, succinic acid, 8-quinolinol, pyridine-2,6-dicarboxylic acid, pyridine, 1,10-tenanthroline, lactic acid, 8-hydroxyquinoline-5-sulfonic acid, glycine, 2,2'-pyridylethylenediamine, aurintricarboxylic acid, xylenol orange, 5-sulfosalicylic acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N,N,N',N'-tetraacetic acid, acetylacetone and their thereof, and their mixtures.

The antiperspirant active ingredients include antiperspirant active ingredients selected from a group consisting of chlorohydroxyaluminium, aluminium chloride, allantoin chlorohydroxyaluminium, aluminium sulfate, zinc oxide, zinc paraphenolsulfonate, and zirconium-aluminium complex produced by reacting zirconyl chloride with aluminium hydroxide and aluminium chlorohydroxide, and their mixtures. The antiperspirant active ingredient as referred to herein is an ingredient that strongly astringes skin to inhibit sweating.

The surfactants include, for example, anionic surfactants such as N-long chain acyl acidic amino acid salts, N-long chain acyl neutral amino acid salts, other N-long chain acyl amino acid salts, N-long chain fatty acid acyl-N-methyltaurine salts, alkyl sulfates and alkylene oxide adducts thereof, fatty acid amide ether sulfates, metal salts and weak base salts of fatty acids, sulfosuccinic acid surfactants, alkylphosphate and alkyleneoxide adducts thereof, and alkyl ether carboxylic acids; nonionic surfactants such as ether surfactants in the form of glycerin ethers and alkylene oxide adducts thereof, ester surfactants in the form of glycerin esters and alkylene oxide adducts thereof, ether ester surfactants such as sorbitan esters and alkylene oxide adducts thereof, polyoxyalkylene fatty acid esters, glycerin esters, fatty acid polyglycerin esters, sorbitan esters, sucrose fatty acid esters, and other ester surfactants, alkyl glucosides, hardened castor oil pyroglutamic acid diesters and ethylene oxide adducts thereof, fatty acid alkanol amides, and other nitrogenous nonionic surfactants; cationic surfactants such as alkyl ammonium chlorides, dialkyl ammonium chlorides, other aliphatic amine salts, quaternary ammonium salts thereof, benzalkonium salts, other aromatic quaternary ammonium salts, and fatty acid acyl arginine esters; and ampholytic surfactants such as carboxybetaine, other betaine surfactants, aminocarboxylic acid surfactants, and imidazoline surfactants.

Various additives include, for example, glycine, alanine, serine, threonine, arginine, glutamic acid, aspartic acid, isoleucine, leucine, valine, and other amino acids; glycerin, ethylene glycol, 1,3-butylene glycol, propylene glycol, isoprene glycol, and other polyhydric alcohols; polyglutamic acid, polyaspartic acid, other polyamino acids, salts thereof, polyethylene glycol, various forms of gum arabic, salts of alginic acid, xanthan gum, hyaluric acid, salts of hyaluric acid, chitin, chitosan, water-soluble chitin, carboxyvinyl polymers, carboxymethyl cellulose, hydroxyethyl cellulose, hydroxypropyl trimethylammonium chloride, polydimethylmethylenepiperidium chloride, polyvinyl pyrrolidone derivative quaternary ammonium salts, cationized proteins, collagen decomposition products and derivatives thereof, acylated proteins, polyglycerin, and other water-soluble polymers; mannitol, other sugar alcohols, and alkylene oxide adducts thereof; ethanol, propanol, and other lower alcohols; plant and animal extracts, nucleic acids, vitamins, enzymes, anti-inflammatory agents, microbicides, preservatives, antioxidants, UV absorbents, chelating agents, antiperspirants, pigments, colorants, oxide dyes, organic and inorganic powders, pH adjusting agents, pearling agents, and moisturizers.

Various powders include, for example, nylon beads, silicone beads, other resin powders, nylon powders, metal fatty acid soaps, yellow iron oxide, red iron oxide, black iron oxide, chromium oxide, cobalt oxide, carbon black, ultramarine blue, Berlin blue, zinc oxide, titanium oxide, zirconium oxide, silicon oxide, aluminum oxide, cerium oxide, titanium mica, boron nitride, barium sulfate, calcium carbonate, magnesium carbonate, aluminum silicate, magnesium silicate, silicon carbide, colorants, lakes, sericite, mica, talc, kaolin, tabular barium silicate, butterfly-shaped barium sulfate, microparticulate titanium oxide, microparticulate zinc oxide, microparticulate iron oxide, acyllysine, acylglutamic acid, acylarginine, acylglycine, and other acylamino acids; and these may be surface-treated with silicone, fluorine compounds, silane coupling agents, silane processed organic titanate, acylated lysine, fatty acids, metal soaps, oils, amino acids, and the like.

Regarding the method for producing the gel composition of the invention, the gelling agent and an oily base material and optionally various additives are heated at 60 to 130° C. with stirring until the mixture gives a uniform solution, and then this is cooled to obtain the intended gel composition. In case where they are dissolved at a low temperature lower than 60° C., the storage stability of the gel may be poor; but when dissolved at a temperature higher than 130° C., then the substances having poor thermal stability may decompose and the volatile components may evaporate.

The gel composition of the invention may be used as cosmetics, aromatics and quasi drugs that contain gel or that are gel-like by themselves irrespective of the shape and the size thereof. Concretely, they include cosmetics such as antiperspirant, face wash, cleansing gel, emulsion, massage cream, cold cream, moisture gel, pack, after-shaving gel, liquid foundation, rouge, cheek, mascara, shampoo, rinse, hair restorer, treatment, hair conditioner, tick, setting lotion, hair cream, hair wax, hair mousse, permanent liquid, hair color, hair manicure, suntan oil, hand soap; aromatics such as aromatics for automobiles, aromatics for restroom use, indoor aromatics; quasi drugs such as medicinal lip cream, poultice, etc. From the viewpoint that the composition can form a strong gel, it is especially favorable for antiperspirant and rouge, more favorable for antiperspirant.

Other features of the invention will become apparent in the course of the following descriptions of exemplary embodiments which are given for illustration of the invention and are not intended to be limiting thereof.

EXAMPLES

Example 1

Production method for N-lauroyl-L-glutamine isopropyl ester 108 g of L-glutamine was dissolved in 343 g of water and 102 g of aqueous 27% sodium hydroxide solution, and cooled to 10° C. 138 g of acetone was added to it, and 152 g of lauroyl chloride and 108 g of aqueous 27% sodium hydroxide solution were dropwise added thereto. The acylation liquid was diluted with 300 g of water, then neutralized with 35 g of 75% sulfuric acid and filtered to obtain a white powdery substance, N-lauroyl-L-glutamine. 72.4 g of thionyl chloride was dropwise added to 424 g of isopropyl alcohol, then 100 g of N-lauroyl-L-glutamine was added thereto and reacted at room temperature for 8.5 hours. The reaction liquid was added to 2.0 L of water to precipitate the intended product, and this was taken out by filtration to obtain a crude product. This was recrystallized repeatedly three times with acetone to obtain 59.1 g of N-lauroyl-L-glutamine isopropyl ester.

$^1$H-NMR (400 MHz, CD$_3$OD, r. t.) δ 5.02 (1H, septet, J=6.2 Hz), 4.35 (1H, dd, J=9.1, 5.1 Hz), 2.32 (2H, t, J=7.8 Hz), 2.25 (2H, t, J=7.3 Hz), 2.14 (1H, m), 1.94 (1H, m), 1.63 (2H, m), 1.40-1.25 (22H, m), 0.92 (3H, t, J=7.1 Hz) ppm.

$^{13}$C-NMR (100 MHz, CD$_3$OD, r. t.) δ 177.9, 176.9, 173.3, 70.6, 54.1, 37.2, 33.5, 33.0, 31.2, 31.0, 30.9, 30.7, 28.6, 27.3, 24.1, 22.4, 14.9 ppm.

ESI-MS (positive) m/z 371.3 [M+H]$^+$, 393.2 [M+Na].

Examples 2 to 4

Melting Temperature of Gelling Agent and Gel Strength of Gel Composition

Table 1 shows the evaluation results of the melting temperature of various 2 wt. % N-acylamino acid monoamide monoalkyl esters and N-acyl-L-amino acid derivatives in liquid paraffin (the unit is ° C.). The gelling agent was added to liquid paraffin to be a concentration of 4% by weight, and heated and dissolved in a oil bath, then left cooled for 15 hours at 23° C. to obtain a gel composition.

The gel strength of the obtained gel composition was measured with a rheometer (FUDOH RHEOMETER HRM-2010-J-CW). 10-φ adaptors for plume and for viscoelasticity were used; and the sample stand speed was 6 cm/min. The evaluation results are shown in Table 1.

The melting point evaluation is as follows: Samples with 110° C. or lower are "OO"; those with from 111 to 130° C. are "O"; those with from 131 to 150° C. are "Δ"; and those with 151° C. or higher are "x". The parenthesized data are melting temperature (° C.).

The gel strength evaluation is as follows: Samples with 601 g/cm$^2$ or more are "OOO"; those with from 501 to 600 g/cm$^2$ are "OO"; those with from 301 to 500 g/cm$^2$ are "O"; those with from 101 to 300 g/cm$^2$ are "Δ"; and those with 100 g/cm$^2$ or less are "x".

TABLE 1

|  |  | Melting Temperature | Gel Strength |
|---|---|---|---|
| Example 2 | N-lauroylglutamine isopropyl ester | ○ | ○○○ |
| Example 3 | N-lauroylglutamine octyl ester | ○○ | ○○ |
| Example 4 | N-lauroylglutamine 2-ethylhexyl ester | ○ | ○ |
| Comparative Example 1 | N-lauroylglutamine cholesteryl ester | ○ | x |
| Comparative Example 2 | N-2-ethylhexylglutamic acid dibutylamide | x | Δ |
| Comparative Example 3 | N$^α$,N$^ω$-dilauroyl-lysine lauryl ester | Δ | x |

From Table 1, it is seen that, as compared with the conventional gelling agents of N-acyl-L-amino acid derivative, the melting temperature of N-acylamino acid monoamide monoalkyl esters in liquid paraffin is low and the gel strength thereof is high.

Examples 5 to 7

Melting Temperature of Gelling Agent and Gel Strength of Gel Composition

In the same manner as in Examples 2 to 4, the melting temperature of various N-acyl acidic amino acid monoamide monoalkyl esters and N-acyl-L-amino acid derivatives in cyclic silicone/octyldodecanol mixed oil, and the gel strength of the gel compositions were measured. The evaluation results are shown in Table 2.

The melting point evaluation is as follows: Samples with 110° C. or lower are "OO"; those with from 111 to 120° C. are "O"; those with from 121 to 140° C. are "Δ"; and those with 141° C. or higher are "x"

The gel strength evaluation is as follows: Samples with 201 g/cm$^2$ or more are "OO"; those with from 101 to 200 g/cm$^2$ are "O"; those with 50 g/cm$^2$ or less are "x".

TABLE 2

|  |  | Melting Temperature | Gel Strength |
|---|---|---|---|
| Example 5 | N-lauroylglutamine isopropyl ester | ○○ | ○○ |
| Example 6 | N-lauroylglutamine octyl ester | ○○ | ○ |
| Example 7 | N-lauroylglutamine 2-ethylhexyl ester | ○○ | ○ |
| Comparative Example 4 | N-lauroylglutamine cholesteryl ester | ○○ | x |
| Comparative Example 5 | N-2-ethylhexylglutamic acid dibutylamide | x | ○○ |
| Comparative Example 6 | N$^α$,N$^ω$-dilauroyl-lysine lauryl ester | Δ | x |

From Table 2, it is seen that, as compared with the conventional gelling agents of N-acyl-L-amino acid derivative, the melting temperature of N-acylamino acid monoamide monoalkyl esters in cyclic silicone/octyldodecanol mixed oil is low and the gel strength thereof is high.

Example 8

Relationship Between the Amount of Various Gelling Agents and Gel Strength

N-lauroyl-L-glutamine isopropyl ester, N-2-ethylhexylglutamic acid dibutyl amide and N$^α$,N$^ω$-dilauroyl-lysine lauryl ester were used as a gelling agent, and liquid paraffin was used as an oily base material, and the relationship between the amount of the gelling agent and the gel strength was investigated.

Gel compositions were produced as follows: Each gelling agent was added to 20 g of liquid paraffin, and dissolved under heat in an oil bath, then left cooled for 15 hours at 23° C. to obtain a gel composition.

The gel strength (g/cm$^2$) of the obtained gel composition was measured with a rheometer (FUDOH RHEOMETER HRM-2010-J-CW). 10-φ adaptors for plume and for viscoelasticity were used; and the sample stand speed was 6 cm/min. The results are shown in FIG. 1, in which:

N-lauroyl-L-glutamine isopropyl ester (◆);
N-2-ethylhexylglutamic acid dibutyl amide (□); and
N$^α$,N$^ω$-dilauroyl-lysine lauryl ester (Δ).

From FIG. 1, it is seen that N-lauroyl-L-glutamine isopropyl ester (ingredient A) increases the gel strength with the increase in its amount added to liquid paraffin. As compared with the conventional gelling agents of N-acyl-L-amino acid derivative, a sufficient strength can be obtained even when a smaller amount of the ingredient A is used, and therefore it is clear at a glance that the gelling potency of the ingredient A is high and the ingredient A has the advantages of broadened formulation latitude and cost reduction.

Examples 9 to 11

Production of Transparent Gel Composition 0.2 g of each gelling agent was added to 20 g of liquid paraffin, and dissolved under heat in an oil bath, then left cooled for 15 hours at 23° C. to obtain a gel composition. The transparency of the obtained gel composition was visually determined. The results are shown in Table 3.

TABLE 3

| Example 9 | N-lauroylglutamine isopropyl ester | semitransparent |
|---|---|---|
| Example 10 | N-palmitoylglutamine isopropyl ester | semitransparent |
| Example 11 | N-lauroylglutamine isopropyl ester/N-palmitoylglutamine isopropyl ester 1/1(wt/wt) mixture | transparent |

As shown in Table 3, mixing the ingredients A each having a different acyl chain length gives a transparent gel composition. It is known that the strength of the gel produced by mixing the gelling agents is higher than the gel strength of the gel composition prepared by the use of a single gelling agent.

Example 12

Production method for 2-(lauroylamino)glutarimide 18.0 g of N-lauroyl-L-glutamine was dissolved in 52.6 mL of dimethylformamide, and 5.50 g of 1-hydroxybenzotriazole was added to it, then 6.90 g of diisopropylcarbodiimide was added thereto and reacted at 50° C. Dimethylformamide was concentrated under reduced pressure, then the reaction mixture was suspended in methanol, the insoluble matter was collected by filtration to obtain 7.88 g of 2-(lauroylamino)glutarimide.

$^1$H-NMR (400 MHz, CD$_3$OD, r. t.): δ 4.65 (1H, dd, J=12.7, 5.4 Hz), 2.79 (1H, ddd, J=17.8, 12.7, 5.6 Hz), 2.68 (1H, ddd, J=17.8, 4.8, 2.7 Hz), 2.28 (2H, td, J=7.5, 2.4 Hz), 2.14 (1H, m), 2.04 (1H, qd, J=12.7, 4.8 Hz), 1.66 (2H, m), 1.40-1.26 (16H, m), 0.92 (3H, t, J=7.0 Hz) ppm.

$^{13}$C-NMR (100 MHz, CD$_3$OD, r. t.): δ 176.8, 175.3, 173.9, 51.4, 37.4, 33.5, 32.5, 31.2, 31.0, 30.9, 30.7, 27.3, 26.2, 24.1, 14.9 ppm.

ESI-MS (positive) m/z 311.2 [M+H]$^+$.

Example 13

Production Method for isopropyl N-lauroyl-2-pyrrolidone-5-carboxylate 10.0 g of isopropyl 2-pyrrolidone-5-carboxylate was dissolved in 58.4 g of toluene, and 13.04 g of lauroyl chloride was added thereto. Further, 6.03 g of triethylamine was dropwise added, and reacted under reflux for 2 hours. Toluene was concentrated under reduced pressure, then the reaction mixture was purified through silica gel column chromatography (hexane/ethyl acetate=5/1 to 3/1) to obtain 3.69 g of isopropyl N-lauroyl-2-pyrrolidone-5-carboxylate.

$^1$H-NMR (400 MHz, CD$_3$OD, r. t.): δ 5.04 (1H, septet, J=6.2 Hz), 4.70 (1H, dd, J=3.6, 9.5 Hz), 2.98 (1H, ddd, J=16.2, 7.8, 6.7 Hz), 2.85 (1H, ddd, J=16.2, 8.1, 6.7 Hz), 2.68 (1H, dt, J=18.6, 9.5 Hz), 2.59 (1H, ddd, J=18.6, 9.5, 4.1 Hz), 2.39 (1H, dq, J=13.2, 9.5 Hz), 2.02 (1H, m), 1.63 (2H, m), 1.40-1.25 (22H, m), 0.92 (3H, t, J=7.6 Hz) ppm.

$^{13}$C-NMR (100 MHz, CD$_3$OD, r. t.): δ 177.0, 176.2, 173.0, 71.0, 60.2, 37.8, 33.5, 33.2, 31.1, 31.0, 30.9, 30.6, 25.8, 24.1, 22.5, 22.3, 22.2, 14.8 ppm.

ESI-MS (positive) m/z 354.3 [M+H]$^+$.

Example 14

Production Method for diisopropyl N-lauroylglutamate 7.24 g of thionyl chloride was gradually and dropwise added to 73.32 g of isopropyl alcohol, then 10.0 g of N-lauroylglutamic acid was added, and reacted at room temperature for 1 day. The reaction liquid was concentrated under reduced pressure to obtain 12.26 g of a white crystal of diisopropyl N-lauroylglutamate.

$^1$H-NMR (400 MHz, CD$_3$OD, r. t.): δ 5.01 (2H, m), 4.39 (1H, m), 2.39 (2H, t, J=7.5 Hz), 2.25 (1H, t, J=7.3 Hz), 2.15 (1H, m), 1.92 (1H, m), 1.63 (2H, m), 1.38-1.23 (28 H, m), 0.92 (3H, t, J=6.8 Hz) ppm.

ESI-MS (positive) m/z 414.3 [M+H]$^+$, 436.2 [M+Na]$^+$.

Examples 15 to 35

Evaluation for Spreadability and Fittability to Skin

Gel compositions were produced in the same manner as in Example 2, for which, however, compounds (I-IV) and oily base materials (cyclic silicone, octyldodecanol) were mixed in a blend ratio shown in Tables 4 to 7.

Evaluation of Gel Strength (Breaking Stress).

The gel strength was evaluated as follows: Samples with 201 g/cm$^2$ or more are "OO"; those with from 101 to 200 g/cm$^2$ are "O"; and those with 50 g/cm$^2$ or less are "x".

Evaluation of Gel Feel.

Four expert panelists tried the gel compositions of Examples and Comparative Examples by applying them to their skin, and evaluated their feel and spreadability, based on two samples with no additive, according to the following evaluation standards.

Spreadability (Evaluated as Five Points of Perfect Scores):

Criteria:
  5: Excellent improvement is seen in spreadability.
  4: Improvement is seen in spreadability.
  3: Some but a little improvement is seen in spreadability.
  2: Average.
  1: Spreadability worsens.

Fittability to Skin (Evaluated as Five Points of Perfect Scores):

Criteria:
  5: Excellent improvement is seen in fittability to skin.
  4: Improvement is seen in fittability to skin.
  3: Some but a little improvement is seen in fittability to skin.
  2: Average.
  1: Fittability to skin worsens.

Samples with the average points of the evaluation result, 4.6 or more are "OOOO"; those with from 4.0 to 4.5 are "OOO"; those with from 3.4 to 3.9 are "OO"; those with from 2.8 to 3.3 are "O"; those with from 2.1 to 2.7 are "Δ"; and those with 2.0 or less are "x". The results are shown in Tables 4, 5 and 6.

TABLE 4

|  |  | Example 15 | Example 16 | Example 17 | Example 18 | Example 19 | Comparative Example 7 |
|---|---|---|---|---|---|---|---|
| Ingredient A | N-lauroylglutamine isopropyl ester | 0.4 | 0.4 | 0.4 | 0.4 | 0.4 | 0.4 |
| Ingredient B | 2-(N'-lauroylamino)-glutarimide | 0.2 |  |  | 0.2 | 0.2 |  |
| Ingredient C | Isopropyl N-lauroyl-2-pyrrolidone-5-carboxylate |  | 0.2 |  | 0.2 |  |  |
| Ingredient D | Diisopropyl N-lauroylglutamate |  |  | 0.2 |  | 0.2 |  |
|  | Cyclic silicone/octyldodecanol = 16/4 | 20 | 20 | 20 | 20 | 20 | 20 |
|  | Breaking stress | ○○ | ○○ | ○○ | ○○ | ○○ | ○○ |
|  | Spreadability | ○○○○ | Δ | Δ | ○○○○ | ○○○○ | x |
|  | Fittability to skin | Δ | ○○○○ | ○○○○ | ○○○○ | ○○○○ | x |

(unit: g)

From Table 4, it is seen that, when the gelling agent comprising the ingredient A and the ingredient B is used, then the produced gel has excellent spreadability, and further, when the gelling agent comprising the ingredient C or the ingredient D in addition to the ingredient A is used, then the fittability to skin of the gel is bettered. Moreover, it is clear that, when the ingredient B, the ingredient C and the ingredient D are all added to the ingredient A, then a gel having good spreadability and good fittability to skin can be produced.

TABLE 5

|  |  | Example 20 | Example 21 | Example 22 | Example 23 | Example 24 | Example 25 | Comparative Example 8 |
|---|---|---|---|---|---|---|---|---|
| Ingredient A | N-lauroylglutamine isopropyl ester | 0.4 | 0.4 | 0.4 | 0.4 | 0.4 | 0.4 | 0.4 |
| Ingredient B | 2-(N'-lauroylamino)-glutarimide | 0.2 | 0.04 | 0.012 | 0.004 | 0.0012 | 0.0004 |  |
|  | Cyclic silicone/octyldodecanol = 16/4 | 20 | 20 | 20 | 20 | 20 | 20 | 20 |
|  | Breaking stress | ○○ | ○○ | ○○ | ○○ | ○○ | ○○ | ○○ |
|  | Spreadability | ○○○○ | ○○○○ | ○○○ | ○○ | ○ | Δ | x |

(unit: g)

From Table 5, it is seen that, even when the ingredient B is added to the ingredient A in an amount of 0.1%, the gel may have spreadability.

TABLE 6

|  |  | Example 26 | Example 27 | Example 28 | Example 29 | Example 30 | Comparative Example 9 |
|---|---|---|---|---|---|---|---|
| Ingredient A | N-lauroylglutamine isopropyl ester | 0.4 | 0.4 | 0.4 | 0.4 | 0.4 | 0.4 |
| Ingredient C | Isopropyl N-lauroyl-2-pyrrolidone-5-carboxylate | 0.2 | 0.002 | 0.004 | 0.002 | 0.0004 |  |
|  | Cyclic silicone/octyldodecanol = 16/4 | 20 | 20 | 20 | 20 | 20 | 20 |
|  | Breaking stress | ○○ | ○○ | ○○ | ○○ | ○○ | ○○ |
|  | Spreadability | ○○○○ | ○○○ | ○○ | ○ | Δ | x |

(unit: g)

From Table 6, it is seen that, even when the ingredient C is added to the ingredient A in an amount of 0.1%, the gel may have spreadability.

TABLE 7

|  |  | Example 31 | Example 32 | Example 33 | Example 34 | Example 35 | Comparative Example 10 |
|---|---|---|---|---|---|---|---|
| Ingredient A | N-lauroylglutamine isopropyl ester | 0.4 | 0.4 | 0.4 | 0.4 | 0.4 | 0.4 |
| Ingredient D | Diisopropyl N-lauroylglutamate | 0.2 | 0.002 | 0.004 | 0.002 | 0.0004 |  |
|  | Cyclic silicone/octyldodecanol = 16/4 | 20 | 20 | 20 | 20 | 20 | 20 |
|  | Breaking stress | ○○ | ○○ | ○○ | ○○ | ○○ | ○○ |
|  | Spreadability | ○○○○ | ○○○ | ○○ | ○ | Δ | x |

(unit: g)

From Table 7, it is seen that, even when the ingredient D is added to the ingredient A in an amount of 0.1%, the gel may have spreadability.

Example 36

Production Method for Gelling Agent 108 g of L-glutamine was dissolved in 343 g of water and 102 g of aqueous 27% sodium hydroxide solution, and cooled to 10° C. 138 g of acetone was added, and 152 g of lauroyl chloride and 108 g of aqueous 27% sodium hydroxide solution were dropwise added. 300 g of the acylation liquid was diluted with water, neutralized with 35 g of 75% sulfuric acid, and filtered to obtain a white powder substance, N-lauroyl-L-glutamine. 367 g of isopropyl alcohol and 30 g of 95% sulfuric acid were added to 101.7 g of the product, and refluxed for 3.5 hours. After solvent removal, 350 g of isopropyl alcohol was added to it, and refluxed for 3 hours. After further solvent removal, 350 g of isopropyl alcohol was added and refluxed for 4 hours. The reaction liquid was left cooled to 35° C., and a white solid was collected by filtration, and dried in vacuum at 50° C. to obtain 73.14 g of a crude crystal of N-lauroyl-L-glutamine isopropyl ester (N-lauroyl-L-glutamine isopropyl ester/2-(lauroylamino)glutarimide/isopropyl N-lauroyl-2-pyrrolidone-5-carboxylate/diisopropyl N-lauryl-L-glutamate (ratio by weight)=100/16/9/16). Further, this was recrystallized from acetone to obtain 30.00 g of a pure crystal of N-lauroyl-L-glutamine isopropyl ester.

Formulation Example 1

Production of Antiperspirant Gel Stick

1) N-lauroyl-L-glutamine isopropyl ester (ingredient A) 3.0 g 2) 2-(lauroylamino)glutarimide (ingredient B) 0.03 g 3) Isopropyl N-lauroyl-2-pyrrolidone-5-carboxylate (ingredient C) 0.03 g 4) 2-hexyldecanol 24.5 g 5) C12-15 benzoate 11.0 g 6) Cyclomethicone D-5 (by Toray Dow Corning, SH245) 32.0 g 7) Aluminium zirconium trichlorohydrex glycine (Westwood Chemical Corporation, Westchlor ZR 30B DM CP-5) 25.0 g The above 1) to 6) were dissolved at 105° C., then cooled to 80° C., and the above 7) was added, and left cooled to room temperature to obtain an antiperspirant gel stick. This product had a sufficient gel strength and was excellent in the spreadability and the fittability to skin.

Formulation Example 2

Production of Cleansing Gel

1) N-palmitoyl-L-glutamine sec-butyl ester (ingredient A) 1.0 g 2) 2-(palmitoylamino)glutarimide (ingredient B) 0.01 g 3) sec-butyl N-palmitoylglutamate (ingredient D) 0.01 g 4) liquid paraffin 20.0 g 5) squalane 2.0 g 6) PEG-30 glyceryl triisostearate (Nippon Emulsion, EMALEX GWIS-320) 7.5 g 7) water 0.5 g The above 1) to 7) were dissolved and left cooled to obtain a cleaning gel. This product had a sufficient gel strength and was excellent in the spreadability and the fittability to skin.

Formulation Example 3

Production of Lip Gloss

1) L-lauroyl-L-glutamine isopropyl ester (ingredient A) 0.05 g 2) 2-(lauroylamino)glutarimide (ingredient B) 0.0005 g 3) diisopropyl N-lauroyl-L-glutamate (ingredient D) 0.0005 g 4) polyisobutene 6.0 g 5) octyldodecanol 5.0 g 6) diisostearyl malate 1.0 g 7) 2-ethylhexanoic acid triglyceride 1.0 g The above 1) to 7) were dissolved and then left cooled to obtain a lip gloss. This product had a sufficient gel strength and was excellent in the spreadability and the fittability to skin.

Formulation Example 4

Production of Antiperspirant Gel Stick

1) N-lauroyl-L-glutamine isopropyl ester crude crystal (Example 36) 3.0 g 2) 2-hexyldecanol 24.5 g 3) C12-15 benzoate 11.0 g 4) Cyclomethicone D-5 (Toray Dow Corning, SH245) 32.0 g 5) Aluminium zirconium trichlorohydrex glycine (Westwood Chemical Corporation, Westchlor ZR 30B DM CP-5) 25.0 g The above 1) to 4) were dissolved at 105° C., then the above 5) was added and left cooled to obtain an antiperspirant gel stick. This product had a sufficient gel strength and was excellent in the spreadability and the fittability to skin.

INDUSTRIAL APPLICABILITY

Using a specific N-acylamino acid monoamide monoalkyl ester as a gelling agent, the invention has made it possible to provide a gel composition having a melting temperature of 100° C. or so, capable of solidifying a wide variety of oil base materials including silicone, and causing no "sweating" while retaining a practical level of gel strength, and further to provide various cosmetics aromatics and quasi drugs, and this is extremely meaningful.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A gelling agent, comprising at least one N-acylamino acid monoamide monoalkyl ester represented by formula (I):

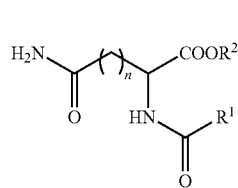

wherein $R^1$ represents a linear or branched hydrocarbon group having from 7 to 17 carbon atoms; $R^2$ represents a linear or branched hydrocarbon group having from 2 to 18 carbon atoms; and n indicates 1 or 2.

2. A gelling agent according to claim 1, which further comprises at least one glutarimide compound represented by formula (II):

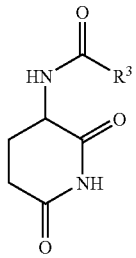

wherein $R^3$ represents a linear or branched hydrocarbon group having from 7 to 17 carbon atoms.

3. A gelling agent according to claim 1, further comprising one or more compounds selected from the group consisting of a pyrrolidone compound represented by formula (III) and an acylglutamic acid diester represented by formula (IV):

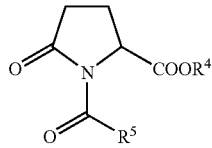

wherein $R^4$ represents a linear or branched hydrocarbon group having from 3 to 6 carbon atoms; and $R^5$ represents a linear or branched, saturated hydrocarbon group having from 7 to 17 carbon atoms,

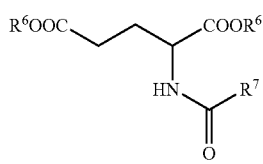

wherein each $R^6$ independently represents a linear or branched hydrocarbon group having from 2 to 6 carbon atoms; and $R^7$ represents a linear or branched hydrocarbon group having from 7 to 17 carbon atoms.

4. A gelling agent, comprising
(A) at least one N-acylamino acid monoamide monoalkyl ester represented by formula (I):

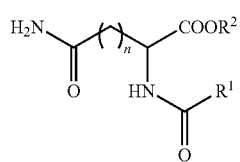

wherein $R^1$ represents a linear or branched hydrocarbon group having from 7 to 17 carbon atoms; $R^2$ represents a linear or branched hydrocarbon group having from 2 to 18 carbon atoms; and n indicates 1 or 2;
(B) at least one glutarimide compound represented by formula (II):

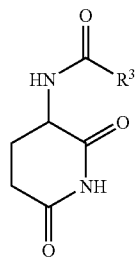

wherein $R^3$ represents a linear or branched hydrocarbon group having from 7 to 17 carbon atoms; and
(C) at least one pyrrolidone compound represented by formula (III):

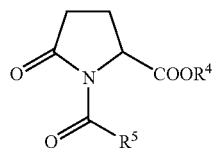

wherein $R^4$ represents a linear or branched hydrocarbon group having from 3 to 6 carbon atoms; and $R^5$ represents a linear or branched, saturated hydrocarbon group having from 7 to 17 carbon atoms.

5. A gelling agent according to claim 4, further comprising:
(D) at least one acylglutamic acid diester represented by formula (IV):

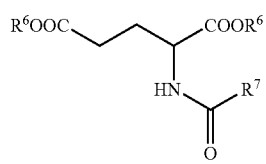

wherein each $R^6$ independently represents a linear or branched hydrocarbon group having from 2 to 6 carbon atoms; and $R^7$ represents a linear or branched hydrocarbon group having from 7 to 17 carbon atoms.

6. A gelling agent according to claim 4, which comprises (A) said at least one N-acylamino acid monoamide monoalkyl ester in an amount of 30% by weight to 99.9% by weight, based on the total weight of said gelling agent.

7. A gelling agent according to claim 4, which comprises (B) said at least one glutarimide compound in an amount of 0.01% by weight to 50% by weight, based on the weight of (A) said at least one N-acylamino acid monoamide monoalkyl ester.

8. A gelling agent according to claim 4, which comprises (C) said at least one pyrrolidone compound in an amount of 0.01% by weight to 1000% by weight, based on the weight of (A) said at least one N-acylamino acid monoamide monoalkyl ester.

9. A gelling agent according to claim 5, which comprises (D) said at least one acylglutamic acid diester in an amount of 0.01% by weight to 1000% by weight, based on the weight of (A) said at least one N-acylamino acid monoamide monoalkyl ester.

10. A gelling agent, comprising
(A) at least one N-acylamino acid monoamide monoalkyl ester represented by formula (I):

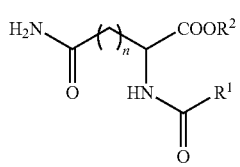

wherein $R^1$ represents a linear or branched hydrocarbon group having from 7 to 17 carbon atoms; $R^2$ represents a linear or branched hydrocarbon group having from 2 to 18 carbon atoms; and n indicates 1 or 2;
(B) at least one glutarimide compound represented by formula (II):

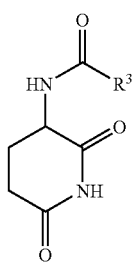

wherein $R^3$ represents a linear or branched hydrocarbon group having from 7 to 17 carbon atoms; and
(D) at least one acylglutamic acid diester represented by formula (IV):

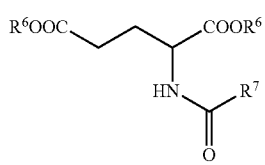

wherein each $R^6$ independently represents a linear or branched hydrocarbon group having from 2 to 6 carbon atoms; and $R^7$ represents a linear or branched hydrocarbon group having from 7 to 17 carbon atoms.

11. A gelling agent according to claim 10, which comprises (A) said at least one N-acylamino acid monoamide monoalkyl ester in an amount of 30% by weight to 99.9% by weight, based on the total weight of said gelling agent.

12. A gelling agent according to claim 10, which comprises (B) said at least one glutarimide compound in an amount of 0.01% by weight to 50% by weight, based on the weight of (A) said at least one N-acylamino acid monoamide monoalkyl ester.

13. A gelling agent according to claim 10, which comprises (D) said at least one acylglutamic acid diester in an amount of 0.01% by weight to 1000% by weight, based on the weight of (A) said at least one N-acylamino acid monoamide monoalkyl ester.

14. A gel composition, comprising a gelling agent according to claim 1 and an oily base material.

15. A gel composition, comprising a gelling agent according to claim 4 and an oily base material.

16. A gel composition, comprising a gelling agent according to claim 5 and an oily base material.

17. A gel composition, comprising a gelling agent according to claim 10 and an oily base material.

18. A gel composition, prepared by mixing a gelling agent according to claim 1 and an oily base material.

19. An N-acylamino acid monoamide monoalkyl ester represented by formula (I):

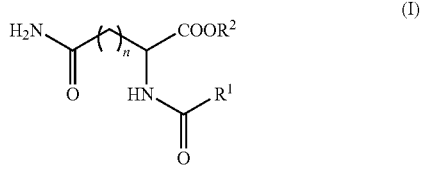

wherein $R^4$ represents a linear or branched hydrocarbon group having from 7 to 17 carbon atoms; $R^2$ represents a linear or branched hydrocarbon group having from 2 to 18 carbon atoms; and n indicates 1 or 2.

20. A pyrrolidone derivative (ingredient C) represented by the following general formula (III):

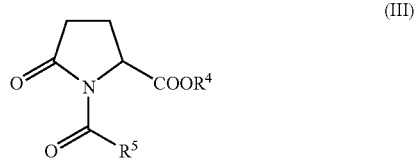

wherein $R^4$ represents a linear or branched hydrocarbon group having from 3 to 6 carbon atoms; and $R^5$ represents a linear or branched, saturated hydrocarbon group having from 7 to 17 carbon atoms.

* * * * *

UNITED STATES PATENT AND TRADEMARK OFFICE
CERTIFICATE OF CORRECTION

PATENT NO. : 7,850,955 B2
APPLICATION NO. : 12/167556
DATED : December 14, 2010
INVENTOR(S) : Keitaro Saito et al.

Page 1 of 1

It is certified that error appears in the above-identified patent and that said Letters Patent is hereby corrected as shown below:

Column 24, line 44, "$R^4$" should read --$R^1$--

Signed and Sealed this
Twenty-second Day of March, 2011

David J. Kappos
*Director of the United States Patent and Trademark Office*